United States Patent
Ryu et al.

(10) Patent No.: US 10,456,041 B2
(45) Date of Patent: Oct. 29, 2019

(54) MEDICAL IMAGING APPARATUS AND METHOD OF CONTROLLING THE SAME

(71) Applicant: SAMSUNG ELECTRONICS CO., LTD., Suwon-si (KR)

(72) Inventors: Jiwon Ryu, Suwon-si (KR); Young Sun Kim, Seoul (KR); Won-Chul Bang, Seongnam-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 1142 days.

(21) Appl. No.: 14/797,882

(22) Filed: Jul. 13, 2015

(65) Prior Publication Data

US 2016/0100760 A1    Apr. 14, 2016

(30) Foreign Application Priority Data

Oct. 13, 2014 (KR) .................... 10-2014-0137903

(51) Int. Cl.
*A61B 5/00* (2006.01)
*A61B 5/055* (2006.01)
*A61B 6/00* (2006.01)
*G06F 19/00* (2018.01)
*G06T 7/33* (2017.01)
(Continued)

(52) U.S. Cl.
CPC .......... *A61B 5/0037* (2013.01); *A61B 5/055* (2013.01); *A61B 5/7445* (2013.01); *A61B 6/405* (2013.01); *A61B 6/482* (2013.01); *A61B 6/5235* (2013.01); *A61B 6/5247* (2013.01); *A61B 90/39* (2016.02); *G06F 19/321* (2013.01); *G06T 7/33* (2017.01); *G16H 40/63* (2018.01); *A61B 5/1114* (2013.01); *A61B 5/6814* (2013.01); *A61B 6/025* (2013.01); *A61B 6/032* (2013.01); *A61B 6/037* (2013.01); *A61B 6/4291* (2013.01); *A61B 6/502* (2013.01); *A61B 2090/3925* (2016.02); *A61B 2090/3954* (2016.02); *A61B 2090/3966* (2016.02); *G01R 33/5608* (2013.01);
(Continued)

(58) Field of Classification Search
CPC .......... A61B 5/0037; A61B 2090/3925; A61B 2090/3954; A61B 2090/3966; A61B 5/055; A61B 5/1114; A61B 5/6814; A61B 5/7445; A61B 6/025; A61B 6/032; A61B 6/037; A61B 6/405; A61B 6/4291; A61B 6/482; A61B 6/502; A61B 6/5235; A61B 6/5247; A61B 90/39; G06T 7/33; G06T 2207/10072; G06T 2207/10132; G06T 2207/30204; G01R 33/5608; G06F 19/321; G16H 40/63
See application file for complete search history.

(56) References Cited

U.S. PATENT DOCUMENTS

| | | | |
|---|---|---|---|
| 2011/0018903 A1* | 1/2011 | Lapstun | G02B 26/06 345/633 |
| 2013/0245461 A1* | 9/2013 | Maier-Hein | A61B 5/0035 600/476 |

* cited by examiner

*Primary Examiner* — Ruth S Smith
(74) *Attorney, Agent, or Firm* — Sughrue Mion, PLLC

(57) ABSTRACT

There are provided a medical imaging apparatus and a method for controlling a medical imaging apparatus. The medical imaging apparatus includes an image registering unit configured to register a pre-imaged medical image with respect to an object based on a first reference point included in the pre-imaged medical image and a second reference point of the object; a location detecting unit configured to detect a user's movement based on the second reference point; and a user interface configured to display a pre-imaged medical image corresponding to the detected movement of the user.

18 Claims, 13 Drawing Sheets

(51) Int. Cl.
  *A61B 90/00* (2016.01)
  *G16H 40/63* (2018.01)
  *A61B 6/03* (2006.01)
  *A61B 6/02* (2006.01)
  *A61B 5/11* (2006.01)
  *G01R 33/56* (2006.01)
(52) U.S. Cl.
  CPC ............... *G06T 2207/10072* (2013.01); *G06T 2207/10132* (2013.01); *G06T 2207/30204* (2013.01)

MEDICAL IMAGING APPARATUS AND METHOD OF CONTROLLING THE SAME

CROSS-REFERENCE TO RELATED APPLICATION

This application claims priority from Korean Patent Application No. 10-2014-0137903, filed on Oct. 13, 2014 in the Korean Intellectual Property Office, the disclosure of which is incorporated herein by reference in its entirety.

BACKGROUND

1. Field

Exemplary embodiments relate to a medical imaging apparatus for registering a pre-imaged medical image with respect to an object and displaying the result and a method for controlling the same.

2. Description of the Related Art

A medical imaging apparatus, such as a magnetic resonance imaging (MRI) apparatus, a computed tomography (CT) apparatus, a single photon emission computed tomography (SPECT) apparatus, a positron emission tomography (PET) apparatus, an ultrasound imaging apparatus or a tomosynthesis apparatus, is an apparatus that non-invasively images an inside of an object by irradiating radiation or a sound wave onto the object and/or by applying a magnetic field to the object.

In particular, medical imaging apparatuses may generate a 2D cross-sectional image and 3D volume data of the object. Since the 3D volume data enables a user to identify morphological characteristics of the inside of the object, it can be beneficially used in the field of diagnosis.

Also, research and development for a method in which a user can easily operate an object while viewing a 3D image in performing any of a simple diagnosis, an invasive procedure, and the like have been actively progressing.

SUMMARY

Exemplary embodiments provide a medical imaging apparatus for registering a pre-imaged medical image to an object and variably displaying the result according to a user's movement, and a method for controlling a medical imaging apparatus.

According to an aspect of one or more exemplary embodiments, there is provided a medical imaging apparatus, including: an image registerer configured to register a pre-imaged medical image with respect to an object based on a first reference point included in the pre-imaged medical image and a second reference point of the object; a location detector configured to detect a user's movement based on the second reference point; and a user interface configured to display a pre-imaged medical image that corresponds to the detected movement of the user.

The first reference point may be recognized by using a marker attached onto a skin of the object when the pre-imaged medical image is generated. The second reference point may be recognized by using a marker attached onto a skin of the object when an image is displayed. The second reference point may be recognized by using a marker on a diagnostic device when an image is displayed.

The location detector may be further configured to detect a change in a direction of the user's sightline, and the user interface may be further configured to change the pre-imaged medical image based on the detected change in the direction of the user's sightline.

The location detector may be further configured to detect a change in a distance between the user and the object, and the user interface may be further configured to enlarge and display the pre-imaged medical image as the detected distance between the user and the object decreases, and to reduce and display the pre-imaged medical image as the detected distance between the user and the object increases.

The user interface may be further configured to display the pre-imaged medical image in at least one from among a cross-sectional image and a cutaway image based on the detected change in the user's sightline.

The user interface may include at least one support frame that is configured to be supported by an ear of the user and to display the pre-imaged medical image in front of an eye of the user.

The user interface may include a transparent display and the pre-imaged medical image may be displayed as an overlay on the object.

The pre-imaged medical image may be a three-dimensional (3D) image and may include at least one from among a magnetic resonance imaging image, a computed tomography image, a single photon emission computed tomography image, a positron emission tomography image and an ultrasound image.

According to another aspect of one or more exemplary embodiments, there is provided a method for controlling a medical imaging apparatus, including: registering a pre-imaged medical image with respect to an object based on a first reference point included in the pre-imaged medical image and a second reference point of the object; detecting a user's movement based on the second reference point; and displaying the pre-imaged medical image that corresponds to the detected movement of the user.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
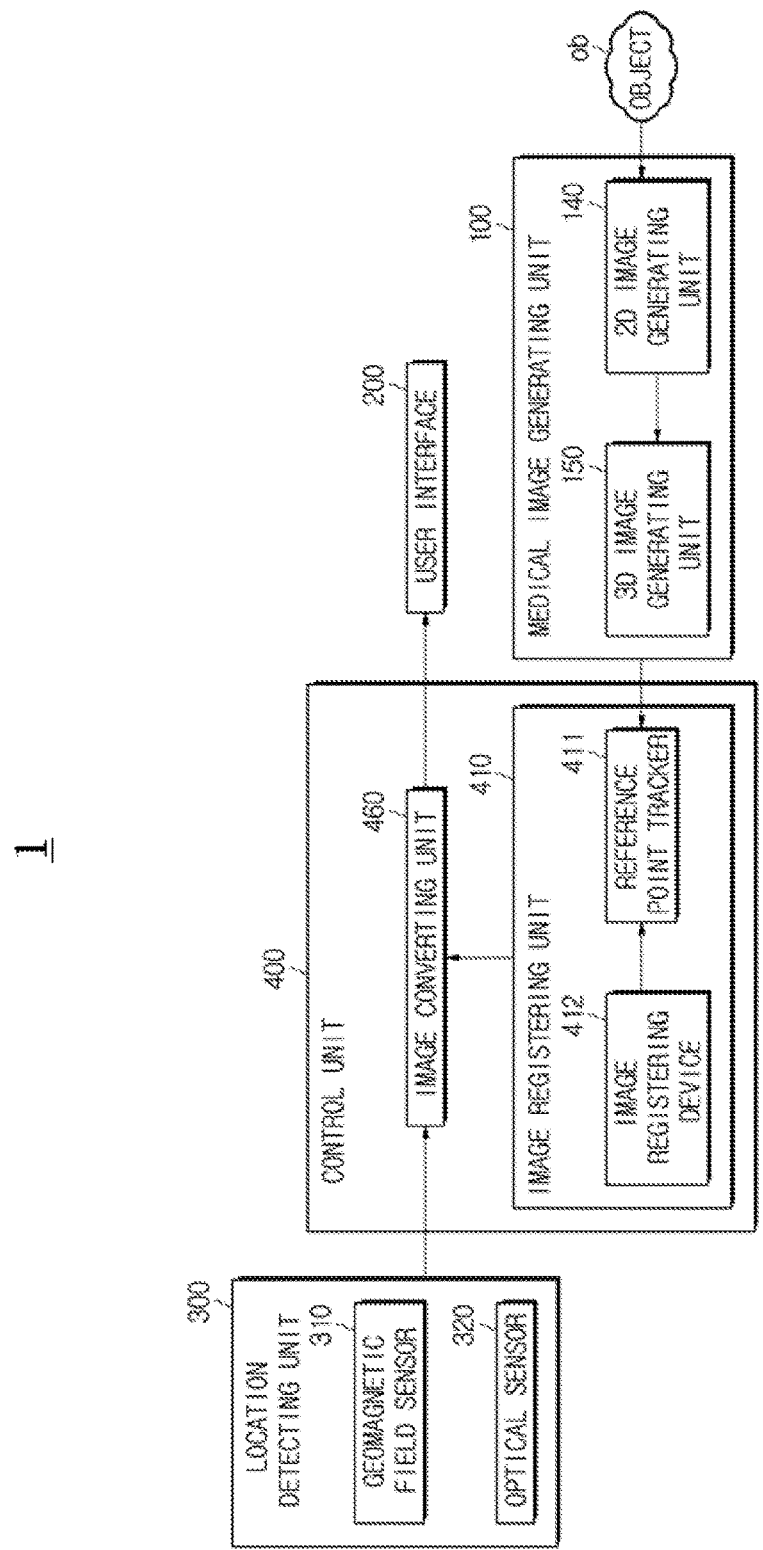
FIG. 1 is a block diagram illustrating a medical imaging apparatus, according to an exemplary embodiment.

Hereinafter, in order to facilitate understanding and reproduction by those of skill in the art, the present inventive concept will be described in detail by explaining exemplary embodiments with reference to the accompanying drawings. When it is determined that detailed explanations of related well-known functions or configurations unnecessarily obscure the gist of the exemplary embodiments, the detailed description thereof will be omitted.

Terms described below are selected by considering functions in the exemplary embodiment and meanings may vary depending on, for example, a user U or operator's intentions or customs. Therefore, in the following exemplary embodiments, when terms are specifically defined, the meanings of terms should be interpreted based on those definitions, and otherwise, should be interpreted based on general meanings recognized by those of ordinary skill in the art.

Also, although the configurations of selectively described aspects or selectively described exemplary embodiments below are illustrated as a single integrated configuration in the drawings, unless otherwise described, it should be understood that these may be freely combined with each other as long as there is no apparent technological contradiction in such combinations for those of ordinary skill in the art.

Hereinafter, exemplary embodiments of a medical imaging apparatus and a method for controlling a medical imaging apparatus will be described with reference to the accompanying drawings.

Hereinafter, an exemplary embodiment of a medical imaging apparatus will be described with reference to FIG. 1.

FIG. 1 illustrates components of the medical imaging apparatus as blocks.

A medical imaging apparatus 1 performs registration of the pre-imaged medical image with respect to an object ob based on a reference point, represents the result in the same coordinate system, and displays the pre-imaged medical image on a user interface 200 according to a user's movement.

Specifically, the medical imaging apparatus 1 may generate an image while a marker is attached to a specific area of the object ob and enable the marker to be displayed on the pre-imaged medical image. The marker displayed on the pre-imaged medical image may be recognized as a first reference point. In addition, the medical imaging apparatus 1 may attach a marker to the same specific area as when imaging is performed in order to generate a second reference point.

Here, the first reference point may include a reference point that is displayed by using the marker at a specific point on the object ob when a medical image is generated, and the second reference point may be a reference point that is displayed by using the marker at a specific point on the object ob when the pre-imaged medical image is displayed. In addition, the second reference point may be a specific point on a diagnostic device or a procedure device that is used by the user to perform diagnosis of or a procedure on the object ob.

In addition, the pre-imaged (pre-operated) medical image herein refers to a three-dimensional (3D) image that is obtained by imaging the object ob before the user displays an image when the procedure or diagnosis is performed. In addition, the term "pre-imaged" corresponds to the term "preliminary." The term "pre-imaged medical image" in this specification is a noun phrase denoting a type of medical image.

In addition, the medical imaging apparatus 1 registers the pre-imaged medical image with respect to the object ob based on the first reference point of the pre-imaged medical image and the second reference point of the object ob viewed by the user. In addition, the medical imaging apparatus 1 detects the user's movement based on the second reference point, and may display the pre-imaged medical image based on the detected movement of the user among the pre-imaged medical images on the user interface 200.

In addition, the medical imaging apparatus 1 may include a medical image generating unit (also referred to herein as a "medical image generator") 100, a location detecting unit (also referred to herein as a "location detector") 300, a control unit (also referred to herein as a "controller") 400, and the user interface 200.

The medical image generating unit 100 generates a medical image of the object ob before an action such as a procedure or diagnosis for displaying a medical image is performed. In addition, the medical image generating unit 100 may include a 2D image generating unit (also referred to herein as a "2D image generator") 140 and a 3D image generating unit (also referred to herein as a "3D image generator") 150.

The 2D image generating unit 140 receives an image signal of a first surface of the object ob obtained in a scan unit (also referred to herein as a "scanner") 110 and generates a 2D image. In addition, the 2D image generating unit 140 receives an image signal of a second surface of the object ob that is obtained by the scan unit 110 while moving, and generates a 2D image of the second surface.

The 3D image generating unit 150 may synthesize 2D images that are generated at a position in a circumferential direction of the scan unit 110 and at a position in a Z-axis direction thereof for each position of the scan unit 110, generate a 3D image, and generate voxel data.

In addition, the 3D image generating unit 150 may generate a 3D model of the object ob, and when a direction of the user's sightline is not a direction in which the scan unit faces the object ob, may display a cross-sectional image based on the user's sightline.

In addition, the medical image generating unit 100 may perform at least one from among computed tomography (CT), single photon emission computed tomography (SPECT) and positron emission tomography (PET) using radiation, tomosynthesis, magnetic resonance imaging (MRI), and ultrasound imaging. Also, two or more methods from among the above imaging methods may be combined and performed.

Figure 8:
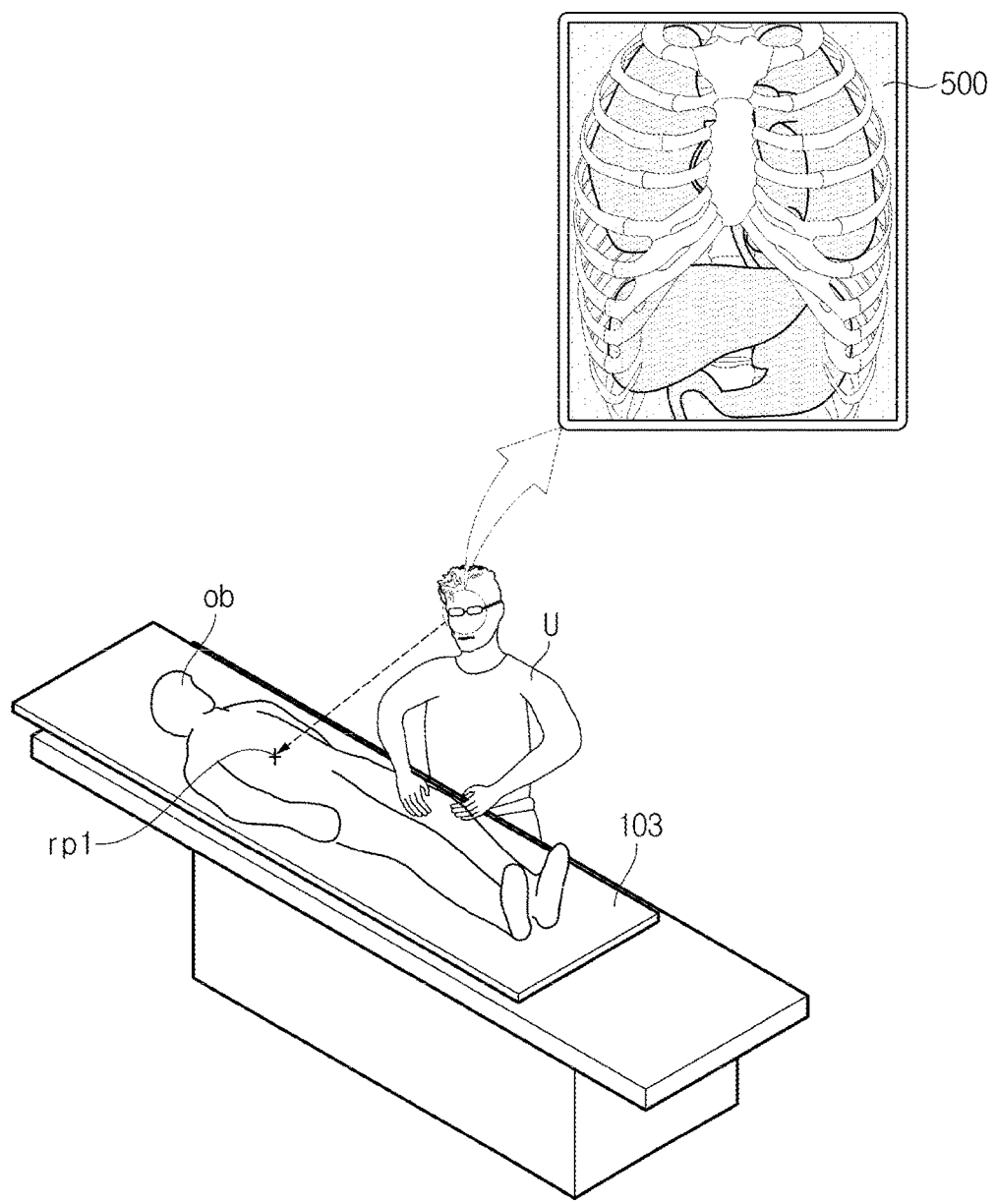
FIG. 8 is a diagram illustrating a concept in which a user registers a pre-imaged medical image with respect to an object and views the result, according to an exemplary embodiment.
Figure 9:
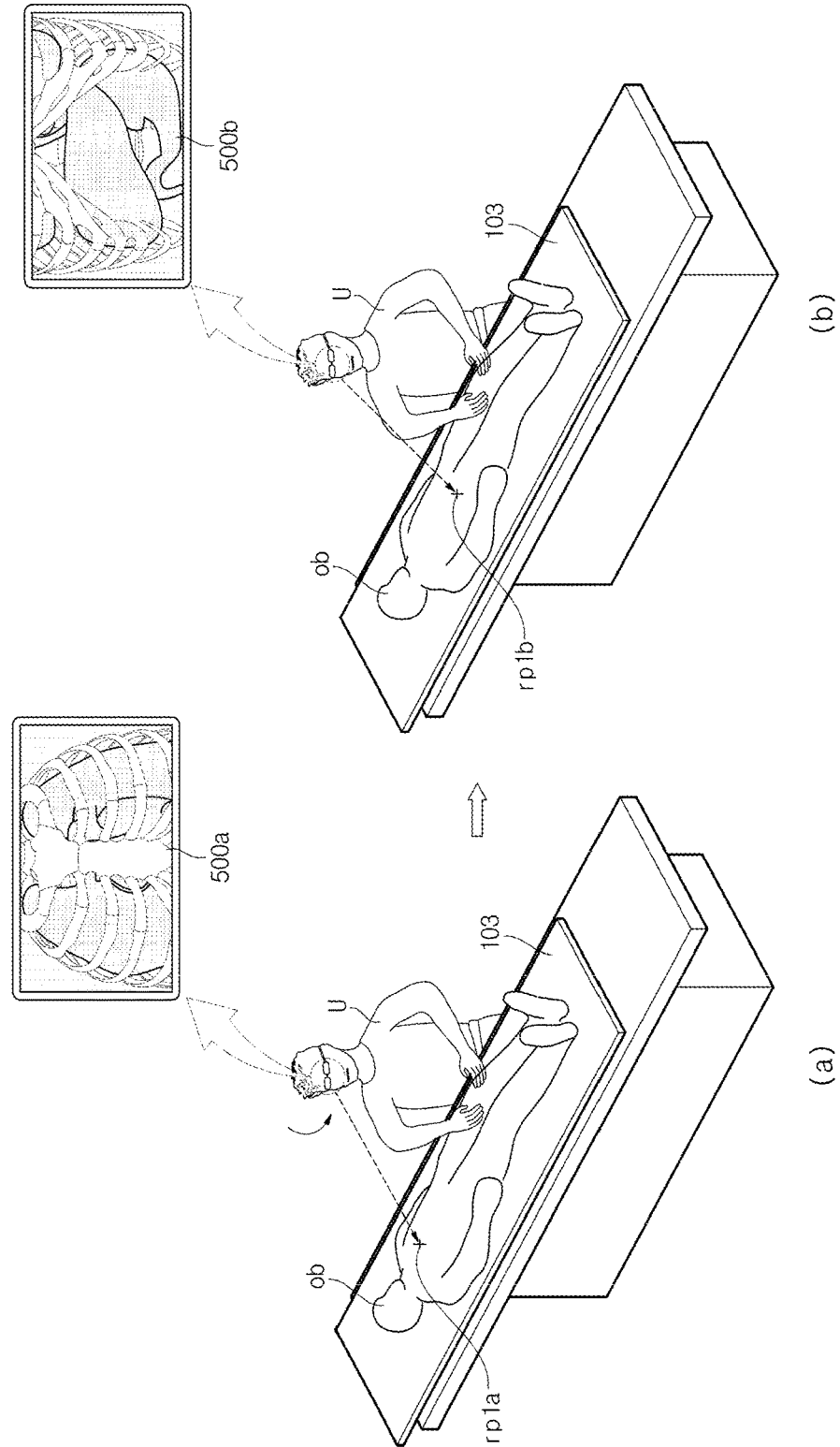
FIG. 9 is a diagram illustrating a concept in which a pre-imaged medical image is changed according to a change in a user's sightline, according to an exemplary embodiment.

The medical image generating unit 100 will be described in detail below with reference to FIGS. 2 to 9. In FIGS. 8 and 9, the user of the medical imaging apparatus 1 is illustrated as user U.

The location detecting unit 300 may detect the user U's movement and determine the pre-imaged medical image to be displayed on the user interface 200. In particular, the location detecting unit 300 may detect a direction of the user U's sightline and a distance thereof and deliver the result to the control unit 400.

Here, the direction of the user U's sightline does not mean a direction of the user U's pupils, but instead refers to a direction in which the user U faces the front. The direction of the user U's sightline may be changed according to movement of the user U's head. Therefore, the direction of the user U's sightline may be a direction of the user interface worn by the user U. In addition, the distance from the user U's eyes to a point at which the user U's sightline reaches a specific point on the object ob. In addition, the distance of the user U's sightline may be a distance from the user interface worn by the user U to a specific point on the object ob. In addition, the user U's movement may correspond to a superordinate concept including a change in the user U's sightline occurring according to movement of the user U's head and the like.

In addition, the location detecting unit 300 may include a geomagnetic field sensor 310 and an optical sensor 320.

The geomagnetic field sensor 310 detects a change in the user U's movement.

Specifically, the geomagnetic field sensor 310 may apply a respective change amount of each of yaw, roll, and pitch values based on a specific point (for example, the second reference point) on the object ob, and may detect a change amount of the user U's sightline. In addition, the geomagnetic field sensor 310 may include a 6-axis sensor configured to measure pitch, yaw and roll and acceleration and/or a 9-axis sensor configured to measure gyro (i.e., angular orientation), acceleration and a geomagnetic field.

The 9-axis sensor detects yaw, roll and pitch values based on a change amount of gyro and acceleration and recognizes a change amount in the sightline. A direction of movement is recognized based on the detected geomagnetic field and the direction of the user U's sightline and a displacement amount thereof may be detected.

The 6-axis sensor detects a change amount of yaw, roll and pitch values based on a change amount of gyro and acceleration, and may recognize a change amount of the sightline. However, designating of an initial point and resetting of yaw, roll, and pitch values may be required.

In addition, the geomagnetic field sensor 310 may be provided on the user interface 200 in the form of eyeglasses and may detect a change in the user U's sightline. In addition, the one geomagnetic field sensor 310 may be provided on the user interface 200, unlike the optical sensor 320.

The optical sensor 320 irradiates light such as infrared (IR) light, visible light or a laser onto the object ob, calculates a reflection time, and detects the user U's movement.

Specifically, the optical sensor 320 detects a distance to the object ob by using a reflection time of light, detects a distance between a plurality of optical sensors 320 and a distance between each of the optical sensors 320 and the object ob, and may detect the direction of the user U's sightline and a distance between the user U and the object ob. In addition, when such detection is performed in real time, a change in the sightline and a change in the distance between the user U and the object ob may be detected.

For example, when two of the plurality of optical sensors 320 are provided at both sides of the user interface 200, based on the user U's sightline that is estimated by using a reference point tracker 411, distances from the two different optical sensors 320 to the object are initially detected, the distances are averaged, and the distance from the user U to the object ob may be calculated. In addition, the optical sensor 320 compares distances detected by the two different optical sensors 320, and may determine that the direction of the user U's sightline is directed toward the optical sensor 320 that is determined to be farther away.

The control unit 400 may deliver a control signal to a component configured to perform each operation such that an operation of the medical imaging apparatus 1 is performed according to an instruction input by the user U. In addition, the control unit 400 controls overall operations and a signal flow of components inside the medical imaging apparatus 1, and performs a data processing function. In addition, the control unit 400 performs control such that power supplied from a power supply unit is delivered to the components inside the medical imaging apparatus 1. In addition, the control unit 400 may register the pre-imaged medical image with respect to the object ob, and may control the user interface 200 so that the pre-imaged medical image corresponding to the object ob is displayed according to the user U's movement.

The control unit 400 serves as a central processing unit, and a type of the central processing unit may be a microprocessor. Here, the microprocessor is a processing device in which an arithmetic logic calculator, a register, a program counter, an instruction decoder, a control circuit and the like are provided in at least one silicon chip.

In addition, the microprocessor may include a graphic processing unit (GPU) for graphic processing of an image or a video. The microprocessor may be implemented as the form of a system on chip (SoC) which includes a core and the GPU. The number of cores included in the microprocessor may be any of one, two, three, four, or a multiple of one thereof.

In addition, the control unit 400 may include a graphic processing board including a GPU, a RAM or a ROM on a separate circuit board that is electrically connected to the microprocessor.

In addition, the control unit 400 may include an image registering unit (also referred to herein as an "image registerer") 410 and an image converting unit (also referred to herein as an "image converter") 460.

The image registering unit 410 registers the pre-imaged medical image with respect to the object ob based on the first reference point included in the pre-imaged medical image and the second reference point based on the object ob.

Specifically, the image registering unit 410 compares a first coordinate system based on the first reference point in the 3D pre-imaged medical image with a second coordinate system based on the second reference point of the object ob. In addition, the image registering unit 410 may register the pre-imaged medical image with respect to the object ob based on the second reference point of the object ob.

In addition, the image registering unit 410 may include the reference point tracker 411 and an image registering device 412.

The reference point tracker 411 may recognize the first reference point included in the pre-set medical image and the second reference point on the object ob.

Specifically, the reference point tracker 411 may recognize a reference point on the medical image or the object ob based on an image in which a shape of the marker for recognizing the reference point is imaged or a signal transmitted from the marker, and may recognize a position of the reference point. In addition, the reference point tracker 411 recognizes a point at which a shape of the object ob is determined not to be included in data based on data of the object ob as a reference point and may recognize the position of the reference point. In addition, any of various methods in which a specific point is recognized on the object ob or the medical image may be used in accordance with an exemplary method of the reference point tracker 411 recognizing the reference point.

The image registering device 412 registers the pre-imaged medical image to the object ob based on the first reference point and the second reference point recognized by the reference point tracker 411.

Specifically, the image registering device 412 may set a coordinate system in which a left and right side of the object ob is set as an X-axis, a front and rear side of the object ob is set as a Y-axis, and an upper and lower side of the object ob is set as a Z-axis based on the first reference point in the 3D modeled pre-imaged medical image. In addition, the image registering device 412 may set a coordinate system in which a left and right side of the object ob is set as an X-axis, a front and rear side of the object ob is set as a Y-axis, and an upper and lower side of the object ob is set as a Z-axis based on the second reference point of the object ob. Here, in the coordinate system of the pre-imaged medical image and the coordinate system of the object ob when the pre-imaged image is displayed, positions of the first reference point and the second reference point are the same, and directions of the X-axis, the Y-axis and the Z-axis are the same. Therefore, the pre-imaged medical image and the object ob may be registered in the same coordinate system. In addition, various methods of registering the pre-imaged medical image to the object ob may be used as an example.

The image converting unit 460 controls the user interface 200 so that the pre-imaged medical image is displayed based on the registration result of the image registering unit 410. In addition, the image converting unit 460 performs control such that the pre-imaged medical image is changed to correspond to the user U's movement detected by the location detecting unit 300 and displayed on the user interface 200.

Specifically, the image converting unit 460 may control the user interface 200 so that the pre-imaged medical image is displayed to correspond to the object ob based on the registration result of the pre-imaged medical image and the object ob in the image registering unit 410. In addition, the image converting unit 460 may control the user interface 200 so that an image to be displayed is displayed in at least one of a cross-sectional image and a cutaway image. In addition, when a display unit is provided in front of the user U's two eyes, the image converting unit 460 may control the user interface 200 so that a cross-section is displayed on one side and a cutaway image is displayed on the other side. In addition, when the display unit is provided in front of the user U's two eyes, the image converting unit 460 may control the user interface 200 so that one side has no displayed image and maintains a transparent form such that the object ob is visible, and the other side displays the pre-imaged medical image in an opaque state when a signal is supplied to a polymer dispersed liquid crystal (PDLC).

In addition, the image converting unit 460 may control the user interface 200 so that the pre-imaged medical image is changed to correspond to the user U's movement as detected by the location detecting unit 300.

Specifically, the image converting unit 460 may detect an area of the object ob that the user U's sightline detected in the location detecting unit 300 reaches, and may display a pre-imaged medical image of a corresponding area. In addition, the image converting unit 460 may detect a change in the direction of the user U's sightline at a predetermined time interval, and may control the user interface 200 so that the pre-imaged medical image is moved in a direction in which his or her sightline moves. In addition, the image converting unit 460 detects a distance between the user U and the object ob at a predetermined time interval, and may control the user interface 200 such that the pre-imaged medical image is enlarged as the distance between the user U and the object ob decreases, and such that the pre-imaged medical image is reduced and displayed as the distance between the user U and the object ob increases.

The user interface 200 displays the pre-imaged medical image based on the user U's movement.

Specifically, the user interface 200 may change the pre-imaged medical image according to a direction of the user U's sightline and display the result, and the user interface 200 may enlarge or reduce the pre-imaged medical image according to a distance between the user U and the object ob and display the result. Detailed description thereof will be provided below with reference to FIG. 9.

In addition, in the user interface 200, at least one support frame is configured to be supported by an ear of the user U, similar to eyeglasses, and at least one display may be provided in front of the user U's eyes. Detailed description thereof will be provided below with reference to FIGS. 10 and 11.

Hereinafter, exemplary embodiments of the medical image generating unit configured to generate the pre-imaged medical image will be described with reference to FIGS. 2 to 7.

Figure 2:
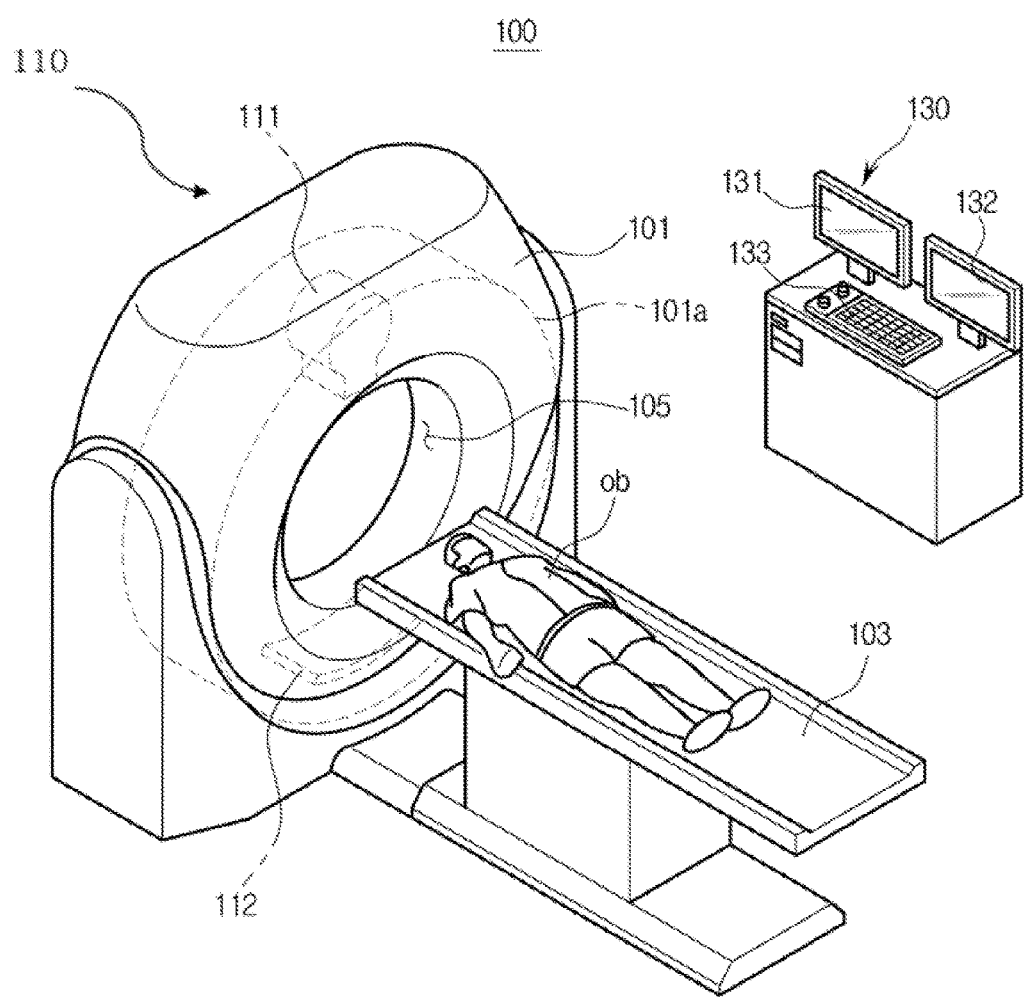
FIG. 2 is a diagram illustrating an appearance of a medical imaging apparatus when a medical image generating unit performs computed tomography, according to an exemplary embodiment.
Figure 3:
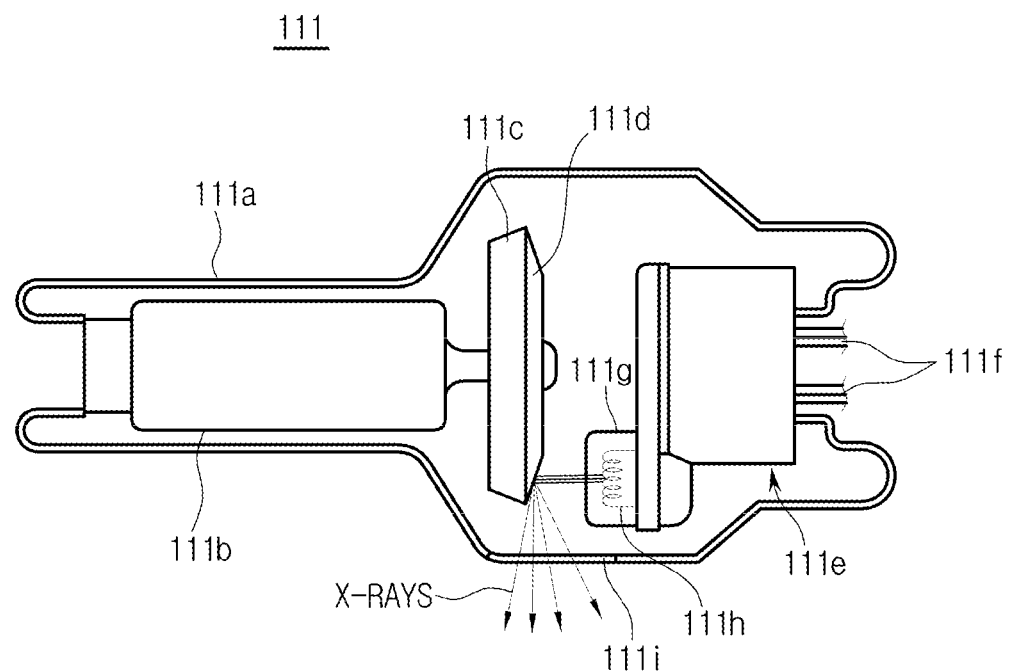
FIG. 3 illustrates an inside of a radiation source when the radiation source irradiates X-rays, according to an exemplary embodiment.

FIG. 2 illustrates an appearance of a medical imaging apparatus when a medical image generating unit performs computed tomography. FIG. 3 illustrates an inside of a radiation source when the radiation source irradiates X-rays.

When the medical image generating unit 100 performs computed tomography, it includes a radiation source 111 configured to irradiate radiation onto the object ob and a radiation detecting module (also referred to herein as a "radiation detector") 112 configured to detect radiation that has propagated through the object ob as illustrated in FIG. 2. The radiation source 111 and the radiation detecting module 112 are mounted in a gantry 101*a* while facing each other. The gantry 101*a* is mounted in a housing 101.

When a patient table 103 on which the object ob is positioned is transferred into a bore 105 formed by the housing 101, the gantry 101*a* in which the radiation source 111 and the radiation detecting module 112 are mounted rotates around the bore 105 at an angle of 180 degrees to 360 degrees, scans the object ob, and obtains projection data.

Radiation includes any of X-rays, gamma rays, alpha rays, beta rays, neutron rays and the like. When the medical image generating unit 100 performs computed tomography, the radiation source 111 may irradiate X-rays.

When the radiation source 111 irradiates X-rays, as illustrated in FIG. 3, the radiation source 111 may be implemented as a diode which includes an anode 111*c* and a cathode 111*e*. The cathode 111*e* includes a filament 111*h* and a focusing electrode 111*g* configured to focus electrons. The focusing electrode 111*g* is also called a focusing cup.

An inside of a glass tube 111*a* is maintained in a high vacuum state of about 10 mmHg, and the filament 111*h* of the cathode is heated to a high temperature to generate thermoelectrons. As an example of the filament 111*h*, a tungsten filament may be used. The filament 111*h* may be heated by applying a current to an electrical conductor 111*f* connected to the filament.

The anode 111*c* is primarily made of copper. A target material 111*d* is applied or disposed at a side facing the cathode 111e. As the target material, a high-resistance material such as any of Cr, Fe, Co, Ni, W or Mo may be used. As a melting point of the target material increases, a focal spot size decreases. Here, a focal point may refer to an effective focal spot. In addition, the target material is inclined at a predetermined angle. As the inclined angle decreases, the focal spot size decreases.

In addition, when a high voltage is applied between the cathode 111e and the anode 111c, thermoelectrons are accelerated and caused to collide with a target material 111d of the anode, and thereby X-rays are generated. The generated X-rays are irradiated to the outside through a window 111i. A beryllium (Be) film may be used as a material of the window. In this case, a filter is positioned in front of or behind the window 111i, and may filter X-rays of a specific energy band.

The target material 111d may be rotated by a rotor 111b. When the target material 111d rotates, a heat accumulation rate per unit area may increase tenfold or more than when the target material is fixed.

The voltage applied between the cathode 111e and the anode 111c of the radiation source 111 is referred to as a tube voltage, and a level thereof may be indicated as peak kilovoltage (kvp). As the tube voltage increases, speeds of the thermoelectrons increase. As a result, energy (i.e., photon energy) generated by the X-rays colliding with the target material increases. A current flowing in the radiation source 111 is referred to as a tube current, and may be indicated as a value, e.g., an average mA. As the tube current increases, the number of thermoelectrons emitted from the filament increases. As a result, a dose of the X-rays (the number of X-ray photons) that are generated by colliding with the target material 111d increases.

Therefore, an amount of energy of X-rays may be controlled by the tube voltage, and an intensity or a dose of X-rays may be controlled by the tube current and an X-ray exposure time. According to a type, a property or a diagnosis purpose of the object ob, an energy and an intensity of X-rays to be irradiated may be controlled.

When the irradiated X-rays have a predetermined energy band, the energy band may be defined by an upper limit and a lower limit. The upper limit of the energy band, that is, a maximum energy of irradiated X-rays, may be adjusted by a level of the tube voltage. The lower limit of the energy band, that is, a minimum energy of irradiated X-rays, may be adjusted by the filter. When X-rays of a low energy band are filtered using the filter, it is possible to increase an average energy of irradiated X-rays.

The radiation detecting module 112 detects X-rays which have penetrated through the object ob, obtains projection data of the object ob, and transmits the obtained projection data to the 2D image generating unit 140. Projection data obtained at any viewpoint represents a 2D projection image of the object ob. While the radiation source 111 and the radiation detecting module 112 rotate, projection data is obtained at a plurality of viewpoints. Therefore, the projection data transmitted to the 2D image generating unit 140 represents a plurality of 2D projection images.

In computed tomography, the radiation detecting module 112 is also referred to as a data acquisition system (DAS). The radiation detecting module 112 may include a plurality of detectors that are mounted in the frame in the form of a one-dimensional (1D) array. Detailed description of a structure of a radiation detector will be provided below.

When the medical image generating unit 100 performs positron emission tomography, a drug to which a radioactive isotope that emits positrons is attached is injected into a body, and then is tracked by using the scan unit 110, thereby identifying a body distribution thereof. In this case, an appearance of the medical image generating unit 100 may be similar to a case in which computed tomography illustrated in FIG. 2 is performed.

The emitted positrons are combined to surrounding electrons in the body, thereby causing the positrons to disappear. As the positrons disappear, gamma rays are emitted in a direction opposite thereto. The emitted gamma rays penetrate through biological tissues. The scan unit 110 includes a radiation detecting module configured to detect gamma rays that have penetrated through biological tissues. Since it is difficult to predict a direction in which gamma rays are emitted, the radiation detecting module in positron emission tomography has a form in which a plurality of detectors are arranged in a circular ring shape surrounding the object ob.

Figure 4:
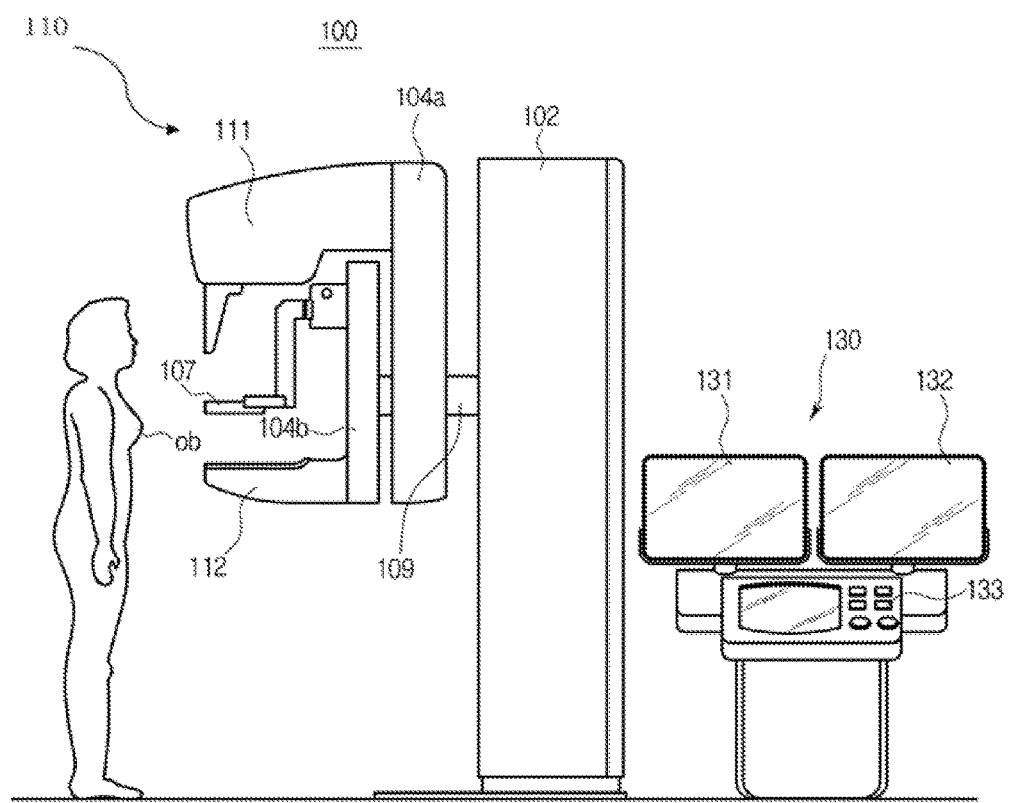
FIGS. 4 and 5 are diagrams of an appearance of a medical imaging apparatus when a medical image generating unit performs tomosynthesis, according to an exemplary embodiment.
Figure 5:
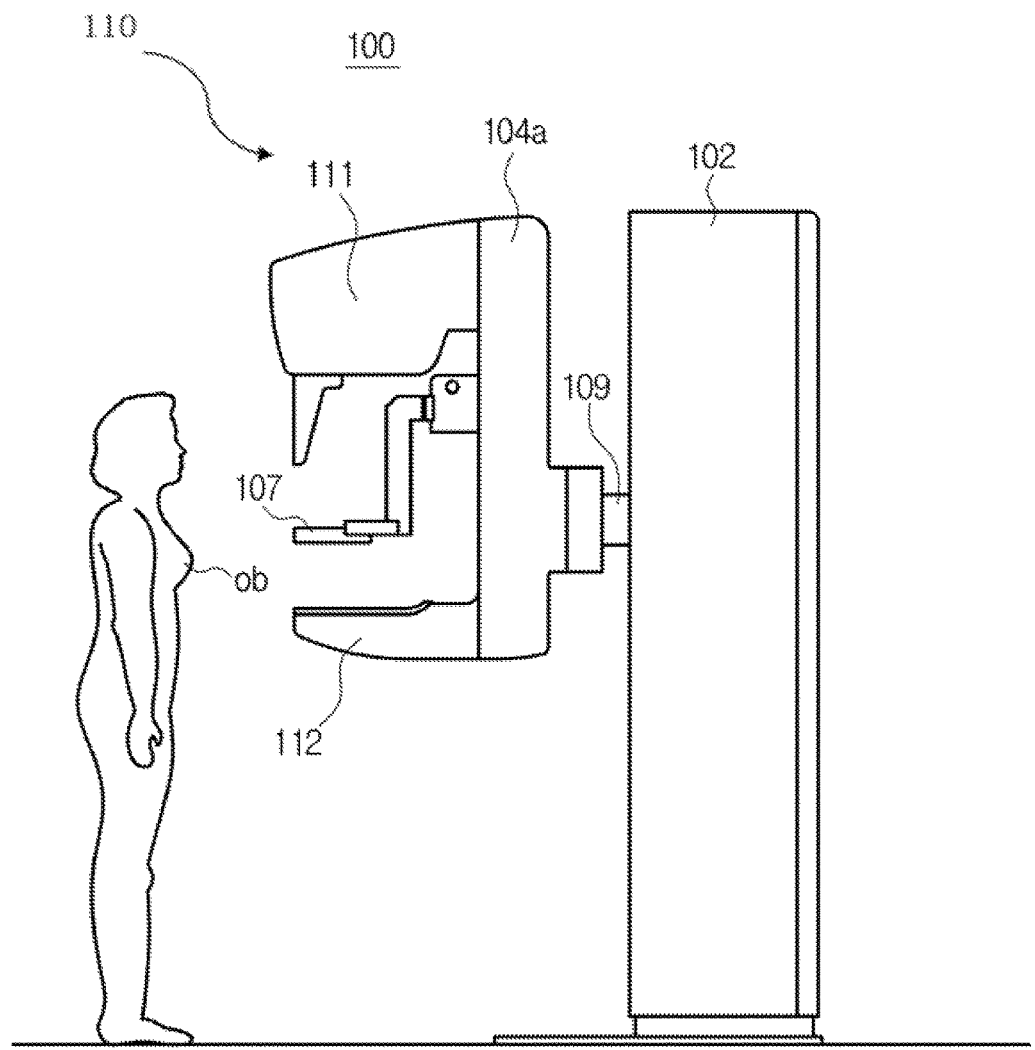
Figure 6:
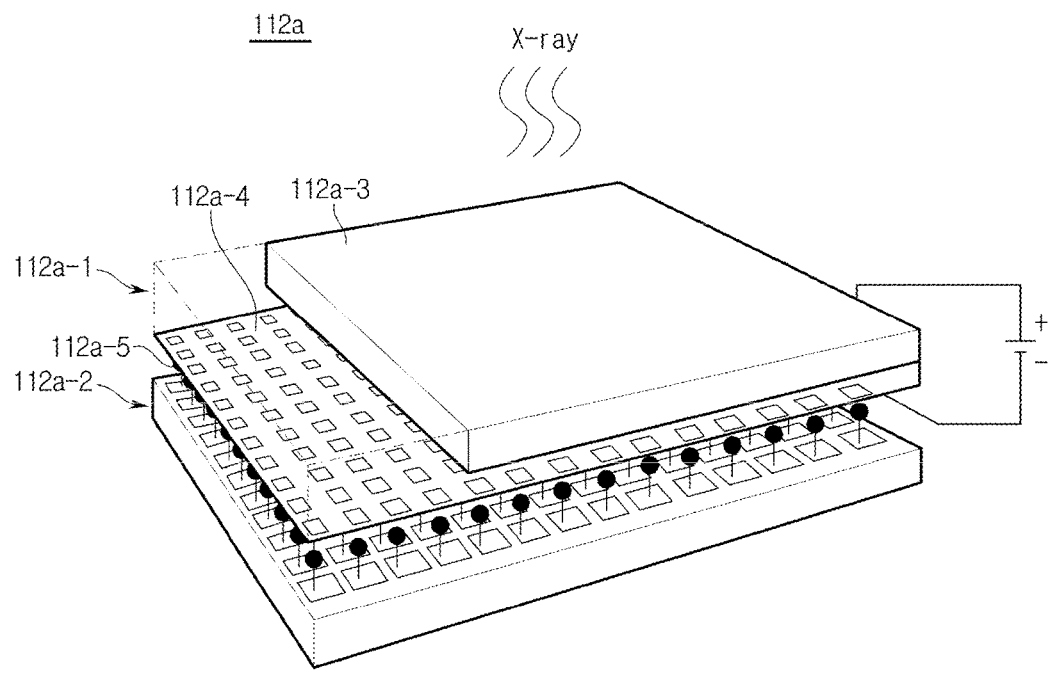
FIG. 6 is a diagram illustrating a structure of a radiation detector configured to detect X-rays, according to an exemplary embodiment.

FIGS. 4 and 5 illustrate an appearance of a medical imaging apparatus when a medical image generating unit performs tomosynthesis. FIG. 6 illustrates a structure of a radiation detector configured to detect X-rays.

When the medical image generating unit 100 performs tomosynthesis, the unit may have a structure as illustrated in FIGS. 4 and 5.

First, as illustrated in FIG. 4, the scan unit 110 includes the radiation source 111, which is configured to generate radiation and to irradiate the radiation onto the object ob, and the radiation detecting module 112, which is configured to detect radiation that have propagated through the object ob. The radiation source 111 may generate X-rays and an internal configuration thereof is the same as above in FIG. 3.

According to characteristics of a breast, which is formed of relatively soft tissues, in order to obtain a clear image, the breast serving as the object ob may be compressed by using a compression paddle 107. The compression paddle 107 may vertically move along a second arm 104b connected to the radiation detecting module 112. When the breast is positioned on the radiation detecting module 112, the compression paddle 107 moves downward and compresses the breast to a predetermined thickness.

When the breast is compressed, X-rays are irradiated from the radiation source 111, and the X-rays that have propagated through the breast are detected by the radiation detecting module 112. The radiation detecting module 112 obtains projection data from the detected X-rays and transmits the data to the 2D image generating unit 140. The scan unit 110 or the radiation source 111 rotates at a predetermined angle, for example, at 20 degrees to 60 degrees, and scans the object ob at a plurality of different viewpoints. Therefore, projection data transmitted to the 2D image generating unit 140 represents a plurality of 2D projection images of the object ob.

In order to scan the object ob at a plurality of different viewpoints, as illustrated in FIG. 4, a first arm 104a to which the radiation source 111 is connected rotates around an axis 109 connected to a housing 102 at a predetermined angle, and may irradiate X-rays onto the object ob. In this case, the radiation detecting module 112 may be fixed and may also rotate. However, when the scan unit 110 has a structure illustrated in FIG. 4, the radiation detecting module 112 is fixed, and only the radiation source 111 rotates.

Also, as illustrated in FIG. 5, when both the radiation source 111 and the radiation detecting module 112 are connected to the first arm 104a and have an integrated structure, the radiation source 111 and the radiation detecting module 112 rotate together when the first arm 104a rotates around the rotation axis 109.

The radiation detecting module 112 includes a radiation detector configured to detect X-rays that have propagated through the object ob, and may also include a grid configured to prevent scattering of X-rays.

The radiation detector may be classified according to any of a material composing method, a method of converting detected X-rays into an electrical signal, and a method of obtaining an image signal.

First, the radiation detector is classified as a case formed of a single element or a case formed of a hybrid element according to the material composing method.

The case formed of the single element corresponds to a case in which a first area in which X-rays are detected to generate an electrical signal and a second area in which the electrical signal is read and processed are formed of a semiconductor of a single material or manufactured as a single process, for example, a case in which a single charge coupled device (CCD) or complementary metal oxide semiconductor (CMOS) serving as a light-receiving element is used.

The case formed of the hybrid element corresponds to a case in which a first area in which X-rays are detected to generate an electrical signal and a second area in which the electrical signal is read and processed are formed of different materials or manufactured as different processes, for example, a case in which X-rays are detected by using a light-receiving element, such as a photodiode or CdZnTe, and an electrical signal is read and processed by using a read out integrated circuit (e.g., CMOS ROIC), a case in which X-rays are detected by using a strip detector and an electrical signal is read and processed by using the CMOS ROIC, a case in which an a-Si or a-Se flat panel system is used, and the like.

In addition, the radiation detector may be classified as a direct converting method or an indirect converting method, according to a method of converting X-rays into an electrical signal.

In the direct converting method, when X-rays are radiated, electron-hole pairs are temporarily generated inside the light-receiving element, electrons move toward the anode and holes move toward the cathode due to an electric field applied to both ends of the light-receiving element, and the X-ray detector converts such movements into an electrical signal. In the direct converting method, a material used in the light-receiving element includes any of a-Se, CdZnTe, $HgI_2$, $PbI_2$ and the like.

In the indirect converting method, a scintillator is provided between the light-receiving element and the radiation source, and when X-rays irradiated from the radiation source react with the scintillator and emit photons having a wavelength of a visible light region, the light-receiving element detects the photons and converts the photons into an electrical signal. In the indirect converting method, a material used in the light-receiving element includes any of a-Si or the like. As the scintillator, any of a thin-film gadolinium oxysulfide (GADOX) scintillator, a micro columnar or needle-shaped cesium iodide (CSI) (T1), or the like is used.

In addition, according to a method of obtaining an image signal, the radiation detector may be classified as a charge integration mode in which electric charges are stored for a predetermined time and a signal is obtained therefrom, or as a photon counting mode in which photons having threshold energy or higher are counted whenever a signal is generated by a single X-ray photon.

Any method from among the above methods may be applied to the radiation detector used in the medical image generating unit 100 according to an exemplary embodiment.

As an example, as illustrated in FIG. 6, a radiation detector 112*a* may include a light-receiving element 112*a*-1 configured to detect X-rays and to convert the detected X-rays into an electrical signal and a readout circuit 121*a*-2 configured to read the electrical signal. Here, the readout circuit 112*a*-2 is formed in a 2D pixel array which includes a plurality of pixel areas. As a material of the light-receiving element 112*a*-1, a single-crystal semiconductor material is used in order to ensure a high resolution, a rapid response time and a high dynamic area at low energy and a low dose. The single-crystal semiconductor material includes any of Ge, CdTe, CdZnTe, GaAs and the like.

The light-receiving element 112*a*-1 may be formed as a PIN photodiode by binding a p-type layer 112*a*-4 in which p-type semiconductors are arranged in a 2D pixel array structure to a bottom of a high resistance n-type semiconductor substrate 112*a*-3. The readout circuit 112*a*-2, which uses a CMOS process, is connected to the light-receiving element 112*a*-1 for each pixel. The CMOS readout circuit 112*a*-2 and the light-receiving element 112*a*-1 may be bonded by using a flip-chip bonding method. The bonding may be performed by using a method in which a bump 112*a*-5 such as solder (PbSn) or indium (In) is formed, reflowed, heated and compressed. However, the above structure is only an example of a radiation detector 112*a*, and the structure of the radiation detector 112*a* is not limited thereto.

Meanwhile, the above structure of the radiation detector 112*a* in FIG. 6 may be applied to the scan unit 110 that performs computed tomography as described above.

Figure 7:
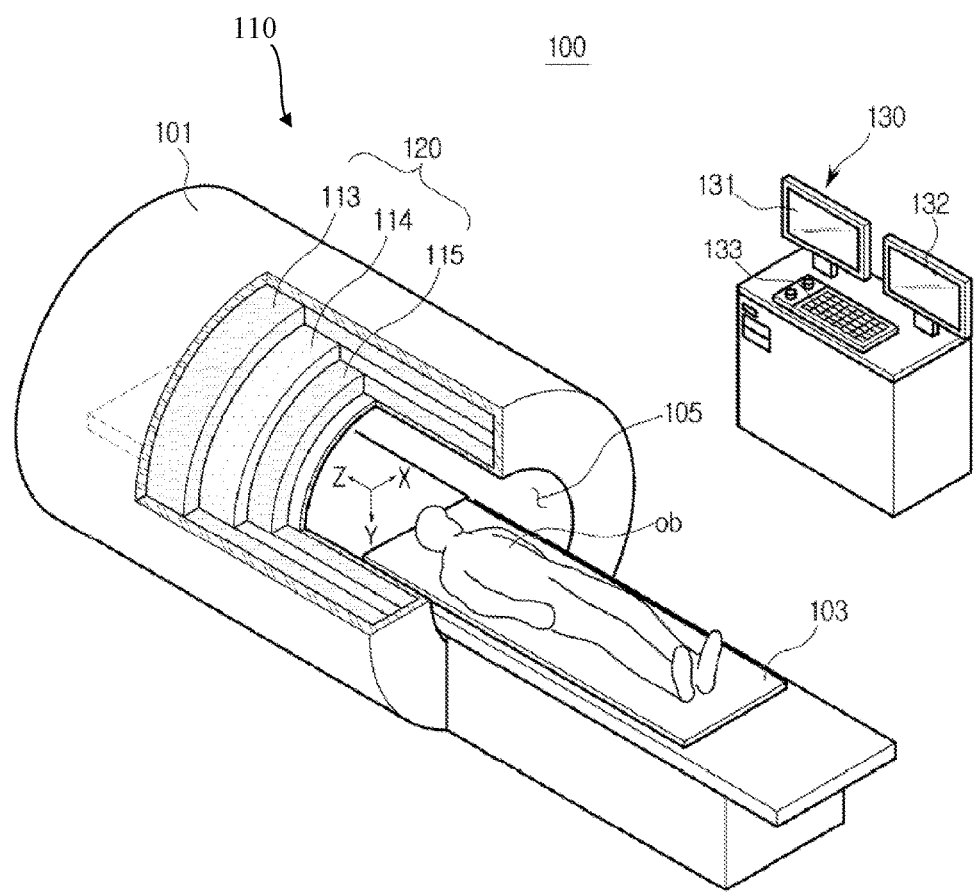
FIG. 7 is a diagram illustrating an appearance when a medical image generating unit uses magnetic resonance, according to an exemplary embodiment.

FIG. 7 illustrates an appearance when a medical image generating unit uses magnetic resonance.

When the magnetic resonance is used, as illustrated in FIG. 7, the medical image generating unit 100 includes the magnet assembly 120 mounted inside the housing 101. The magnet assembly 120 includes a static field coil 113 configured to form a static field inside the bore 105 formed by the housing 101, a gradient coil 114 configured to generate a gradient in the static field and form a gradient field, and a radio frequency (RF) coil 115 configured to apply an RF pulse to excite an atomic nucleus and receive an echo signal from the atomic nucleus. In particular, when the patient table 103 on which the object ob is positioned is transferred into an internal space of the bore 105, the static field, the gradient field and the RF pulse are applied to the object ob, the atomic nucleus of the object ob excites, and an echo signal is generated therefrom. The RF coil 115 receives the echo signal and transmits the signal to the 2D image generating unit 140. When the scan unit 110 performs magnetic resonance imaging, the echo signal received by the RF coil 115 becomes projection data of the object ob.

Meanwhile, although not illustrated, when the medical image generating unit 100 performs magnetic resonance imaging, the medical image generating unit 100 may include a controller configured to control an intensity and a direction of the static field, design a pulse sequence, and accordingly control the gradient coil 114 and the RF coil 115.

Referring again to FIGS. 2 to 7, the medical image generating unit 100 includes a host device 130 configured to perform overall control of an operation of the scan unit 110, image processing, and the like. The host device 130 may include a 2D display unit (also referred to herein as a "2D display device" and/or as a "2D display") 131 and a 3D display unit (also referred to herein as a "3D display device" and/or as a "3D display") 132, and may also include an input unit 133 configured to receive a control instruction from the user U.

The medical image generating unit 100 has been described above in detail with reference to FIGS. 2 to 7.

Hereinafter, the user interface 200, the location detecting unit 300 and the control unit 400 will be described in detail.

Hereinafter, an exemplary embodiment of displaying a pre-imaged medical image will be described with reference to FIGS. 8 and 9.

FIG. 8 illustrates a concept in which a user registers a pre-imaged medical image with respect to an object and views the result.

As illustrated in FIG. 8, when the user U views the second reference point rp1, the medical imaging apparatus 1 may perform registration in the same coordinate system based on the first reference point of the pre-imaged medical image and the second reference point rp1 of the object ob. In addition, the medical imaging apparatus 1 may display a pre-imaged medical image of an area of the object ob that the user U currently views among the registered pre-imaged medical image on the display unit of the user interface 200 in a cutaway image. Therefore, as illustrated in FIG. 8, the pre-imaged medical image of the object ob, as illustrated in a cutaway image, may be displayed on a see-through image screen 500 of the user interface.

FIG. 9 illustrates a concept in which a pre-imaged medical image is changed according to a change in a user's sightline.

As described in FIG. 8, the medical imaging apparatus 1 may register the pre-imaged medical image generated by the medical image generating unit 100 to the object ob and display the pre-imaged medical image so as to correspond to a specific area of the object ob viewed by the user U.

In addition, in the medical imaging apparatus 1, according to a change in the user U's sightline, a medical image to be displayed may be changed.

Specifically, as illustrated in drawing (a) on the left side of FIG. 9, when the user U views an upper side of the chest of the object ob at reference point rp1a, the location detecting unit 300 may detect the user U's sightline and display a pre-imaged medical image 500a of the upper side of the chest.

Conversely, as illustrated in drawing (b) on the right side of FIG. 9, when the user U views the upper side of the chest of the object ob at reference point rp1a and then changes his or her sightline to a lower side of the chest of the object ob at reference point rp1b, the location detecting unit 300 may detect the user U's sightline, and a pre-imaged medical image 500b of the lower side of the chest may be displayed on the user interface 200.

Therefore, when the pre-imaged medical image is changed and displayed according to the user U's sightline, it is convenient for the user U to perform a procedure or diagnosis.

Hereinafter, exemplary embodiments of a user interface will be described with reference to FIGS. 10 and 11.

Figure 10:
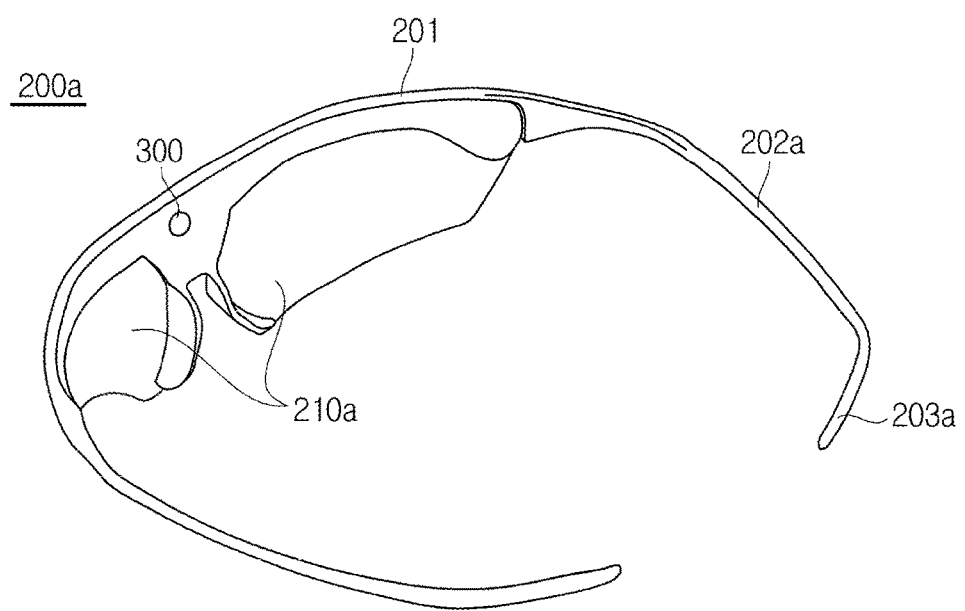
FIG. 10 is a diagram illustrating an appearance of a user interface, according to an exemplary embodiment.

FIG. 10 illustrates an appearance of a user interface, according to an exemplary embodiment.

The user interface 200a has the form of eyeglasses, is supported by the ears of the user U, and may display the pre-imaged medical image in front of the user U's eyes.

In addition, the user interface 200a may include a main frame 201, a support frame 202a, a support ring 203a, a display unit 210a and the location detecting unit 300.

The main frame 201 supports a front of the user interface 200a and is connected to the support frame 202a and the display unit 210a. In addition, the main frame 201 may deliver supporting power to an ear of the user U via the support frame 202a, fix the display unit 210a, and deliver an image control signal to the display unit 210a.

The support frame 202a and the support ring 203a may be connected to both sides of the main frame 201, deliver the force of gravity of the user interface 200a to the ear of the user U, and support the user interface 200a. In addition, the support frame 202a and the support ring 203a may be made of any of a rigid metal, plastic or a carbon material. In addition, the support ring 203a has a curve such that it can be mounted on the ear of the user U and may be bent toward an inner side surface.

The display unit 210a displays the pre-imaged medical image that is processed by the control unit 400.

The display unit 210a may include any of a flat display unit, a curved display unit that is a screen having a curvature, and/or a flexible display unit that is capable of adjusting a curvature.

The display unit 210a has an output resolution of, for example, high definition (HD), full HD or ultra HD.

In addition, the display unit 210a may use a transparent display and overlay the pre-imaged medical image on the object ob. In this case, as a method in which the pre-imaged medical image is displayed on the display unit 210a, a light source may be provided in front of a display, an image of light radiated onto a transparent display such as a head up display (HUD) or a helmet mounted display (HMD) is formed, and the image may be displayed.

In addition, the display uses a polymer dispersed liquid crystal (PDLC) whose transparency varies according to whether an electrical signal is applied, and as necessary, may overlay the pre-imaged medical image on the object ob or block the object ob and display only the pre-imaged medical image.

The location detecting unit 300 is provided on the main frame 201, detects the user U's movement (specifically, a change in the user U's sightline and a distance between the user U and the object ob), and delivers the detected value to the control unit 400.

A function, a type and the like of the location detecting unit 300 may be the same as or different from those in the location detecting unit 300 as described above with respect to FIG. 1.

Figure 11:
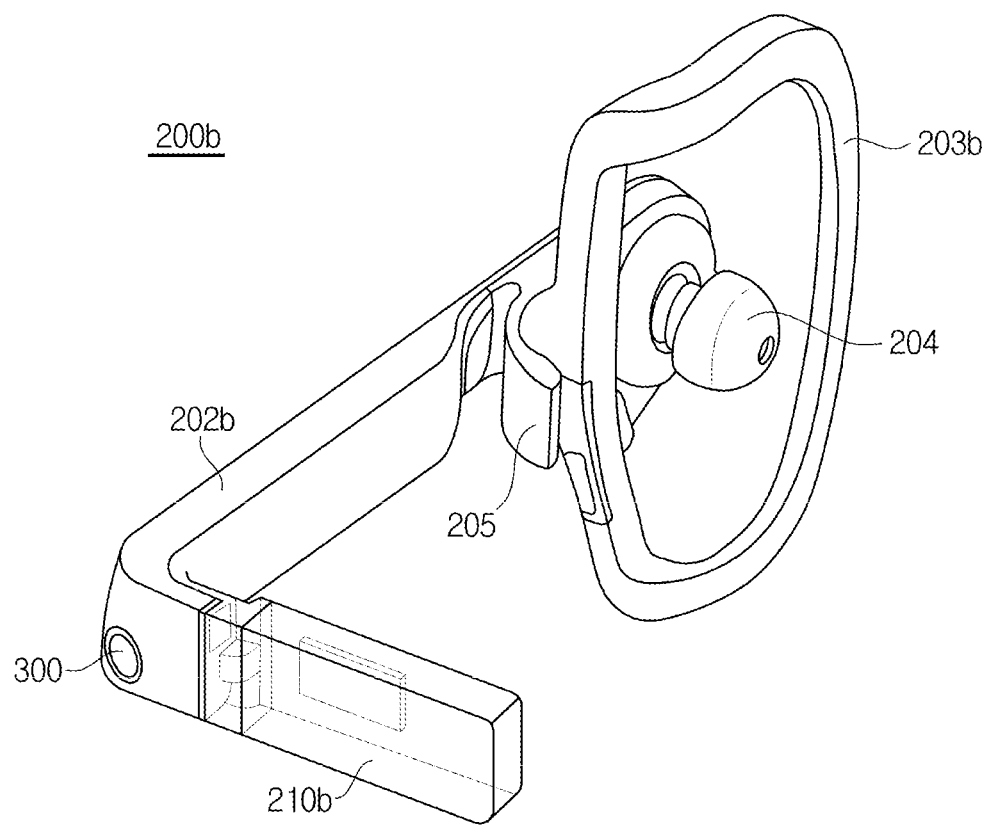
FIG. 11 is a diagram illustrating an appearance of a user interface, according to another exemplary embodiment.

FIG. 11 illustrates an appearance of a user interface, according to another exemplary embodiment.

As illustrated in FIG. 11, the user interface 200b may have the form of an eyeglass that is supported by only an area near one eye of the user U.

In addition, the user interface 200b may include a support frame 202b, a support ring 203b, a support protrusion 205, an earphone 204, a display unit 210b and the location detecting unit 300.

The support frame 202b is connected between the display unit 210b and the support ring 203b, supports the force of gravity of the user interface 200b, and delivers the force to the ear of the user U. The support ring 203b has an annular structure covering a contour of an ear of the user U, is put on the ear of the user U, delivers the force of gravity of the user interface 200b delivered by the support frame 202b to the ear, and supports the user interface 200b. The support protrusion 205 is provided in front of the support ring 203b and provides a protrusion such that the user interface 200b does not rotate while the ear of the user U is inserted to the support ring 203b. In addition, the support frame 202b, the support ring 203b and the support protrusion 205 may be made of any of a rigid metal, plastic or a carbon material.

When the earphone 204 is inserted into the ear of the user U and the user U performs diagnosis of or a procedure on the object ob, a sound user interface 200b which is configured to convey a sound such as a beep and voice guidance may be provided. As illustrated in FIG. 11, the earphone 204 may be any of an in-ear type, an on-ear type or an around-ear type.

The display unit 210b may have one side connected to the support frame 202b, receive the image control signal, and display the pre-imaged medical image.

A function, a type and the like of the display unit 210b may be the same as or different from those in the display unit 210a as illustrated in FIG. 10.

The location detecting unit 300 is provided on the support frame 202b, detects the user U's movement (specifically, a change in the user U's sightline and a distance between the user U and the object ob), and delivers the detected value to the control unit 400.

A function, a type and the like of the location detecting unit 300 may be the same as or different from those in the location detecting unit 300 described above with respect to FIG. 1.

Hereinafter, another exemplary embodiment of displaying a pre-imaged medical image will be described with reference to FIG. 12.

Figure 12:
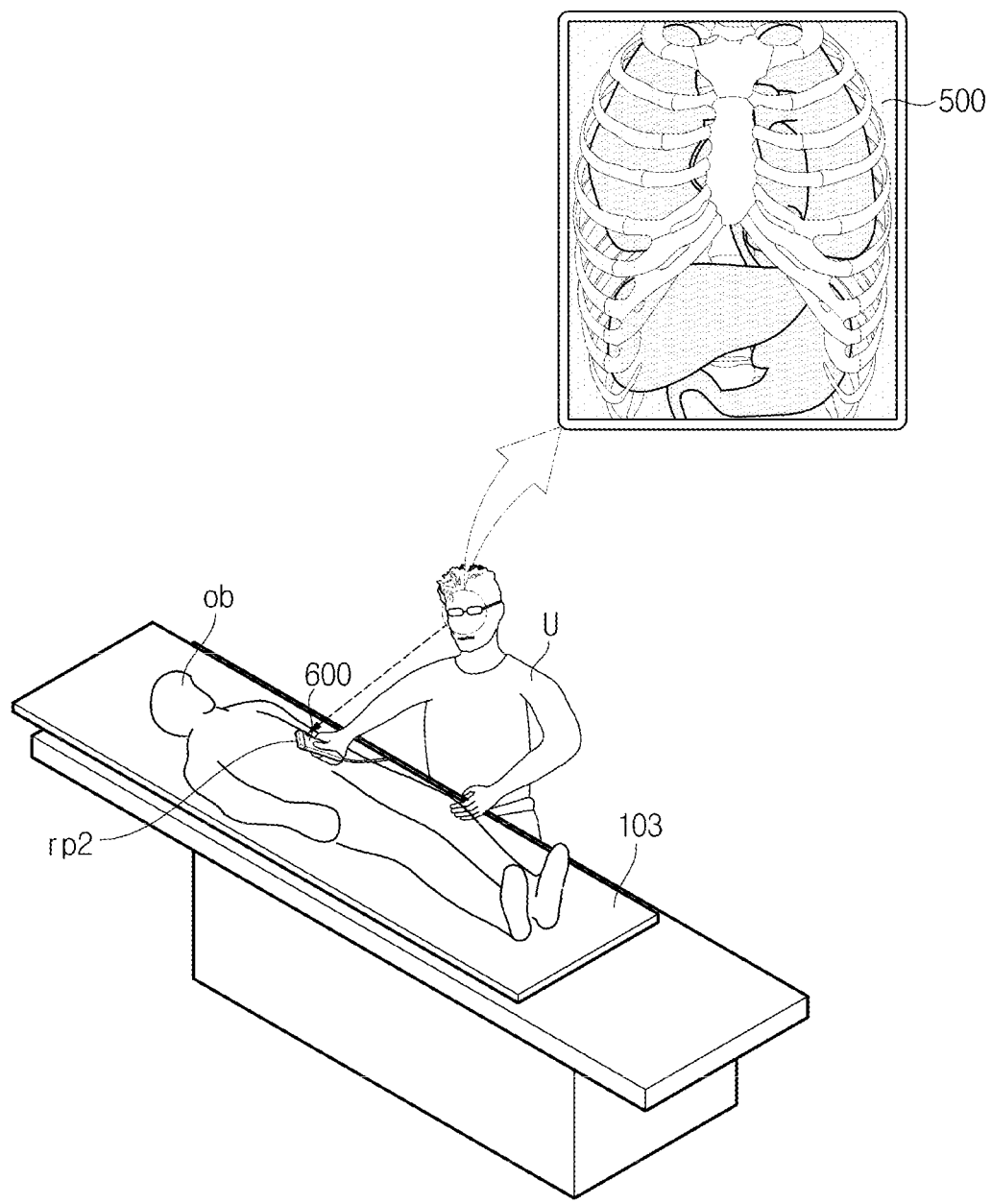
FIG. 12 is a diagram illustrating a concept in which a user registers a pre-imaged medical image with respect to an object and views the result, according to another exemplary embodiment.

FIG. 12 illustrates a concept in which a user registers a pre-imaged medical image with respect to an object ob and views the result.

As illustrated in FIG. 12, when the user U views the second reference point rp2 at an end of an ultrasound probe, the medical imaging apparatus 1 may perform registration in the same coordinate system based on the first reference point of the pre-imaged medical image and the second reference point rp2 of the probe. In addition, the medical imaging apparatus 1 may display a pre-imaged medical image of an area 600 of the object ob at which the probe is currently positioned among the registered pre-imaged medical image on the display unit of the user interface 200 in a cutaway image. Therefore, as illustrated in FIG. 12, the pre-imaged medical image of the object ob in a cutaway image may be displayed on the see-through image screen 500 of the user interface 200.

The configuration of the medical imaging apparatus has been described above.

Hereinafter, a method of controlling a medical imaging apparatus will be described with reference to FIG. 13.

Figure 13:
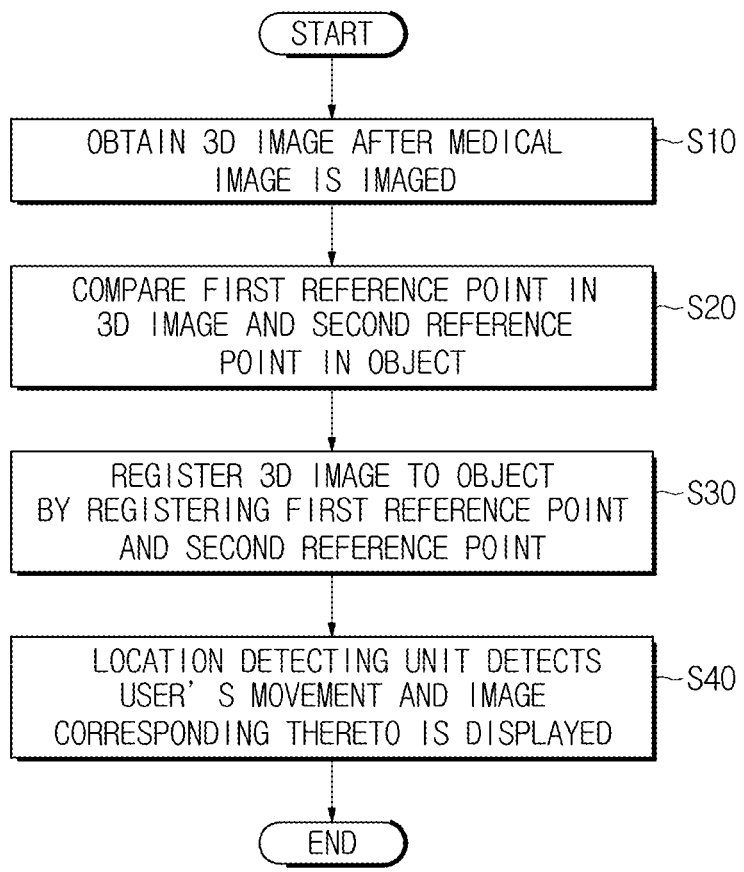
FIG. 13 is a flowchart illustrating a method for registering a pre-imaged medical image with respect to an object and displaying the result, according to an exemplary embodiment.

FIG. 13 is a flowchart illustrating a method for registering a pre-imaged medical image with respect to an object and displaying the result.

First, in operation S10, the medical image generating unit 100 generates a 2D medical image by using an apparatus such as a magnetic resonance imaging (MRI) apparatus, a computed tomography (CT) apparatus, a single photon emission computed tomography (SPECT) apparatus, a positron emission tomography (PET) apparatus, an ultrasound imaging apparatus and a tomosynthesis apparatus, and obtains a 3D medical image by synthesizing and 3D modeling the generated image.

Then, in operation S20, the first reference point included in the 3D medical image and the second reference point of the object ob are recognized and compared. In addition, in operation S30, the control unit 400 performs registration of the first reference point and the second reference point and registers the 3D medical image to the object ob.

Then, in operation S40, the location detecting unit 300 detects the user U's movement and displays a medical image which corresponds to the movement among the 3D image.

According to the medical imaging apparatus and the method of controlling a medical imaging apparatus, the pre-imaged medical image is registered with respect to the object, and the pre-imaged medical image is displayed so as to correspond to the user's movement. Therefore, the user is able to intuitively recognize the pre-imaged medical image.

The above description is only an example describing a technological scope of the present inventive concept. Various changes, modifications, and replacements may be made without departing from the spirit and scope of the present inventive concept by those skilled in the field of medical devices. Therefore, the exemplary embodiments disclosed in the above and the accompanying drawings should be considered in a descriptive sense only and not for limiting the technological scope. The technological scope of the present inventive concept is not limited by these exemplary embodiments and the accompanying drawings. The spirit and scope of the present inventive concept should be interpreted by the appended claims and encompass all equivalents falling within the scope of the appended claims.

What is claimed is:

1. A medical imaging apparatus, comprising:
   at least one processor configured to register a pre-imaged medical image with respect to an object based on a first reference point included in the pre-imaged medical image and a second reference point of the object;
   a location detector configured to detect movement of a user based on the second reference point; and
   a user interface configured to display an image of the pre-imaged medical image that corresponds to the detected movement of the user,
   wherein the at least one processor is further configured to recognize the second reference point by detecting a marker on a diagnostic device when the pre-imaged medical image is displayed.

2. The medical imaging apparatus according to claim 1, wherein the first reference point is recognized by using a marker attached onto a skin of the object when the pre-imaged medical image is generated.

3. The medical imaging apparatus according to claim 1, wherein the location detector is further configured to detect a change in a direction of a sightline of the user, and
   the user interface is further configured to change the image based on the detected change in the direction of the sightline of the user.

4. The medical imaging apparatus according to claim 3, wherein the user interface is further configured to display the image in at least one from among a cross-sectional image and a cutaway image based on the detected change in the sightline of the user.

5. The medical imaging apparatus according to claim 1, wherein the location detector is further configured to detect a change in a distance between the user and the object, and
   the user interface is further configured to enlarge and display the image as the detected distance between the user and the object decreases, and to reduce and display the image as the detected distance between the user and the object increases.

6. The medical imaging apparatus according to claim 1, wherein the user interface includes at least one support frame that is configured to be supported by an ear of the user and to display the image in front of an eye of the user.

7. The medical imaging apparatus according to claim 6, wherein the user interface includes a transparent display and the image is displayed as an overlay on the object.

8. The medical imaging apparatus according to claim 1, wherein the pre-imaged medical image is a three-dimensional (3D) image and includes at least one from among a magnetic resonance imaging image, a computed tomography image, a single photon emission computed tomography image, a positron emission tomography image and an ultrasound image.

9. The medical imaging apparatus according to claim 1, wherein the user interface is configured to display an image of the pre-imaged medical image that corresponds to an area of the object at which the diagnostic device is positioned, in response to the marker on the diagnostic device being detected by the at least one processor.

10. A method for controlling a medical imaging apparatus, comprising:
registering a pre-imaged medical image with respect to an object based on a first reference point included in the pre-imaged medical image and a second reference point of the object;
detecting movement of a user based on the second reference point;
displaying an image of the pre-imaged medical image that corresponds to the detected movement of the user; and
recognizing the second reference point by detecting a marker on a diagnostic device when the pre-imaged medical image is displayed.

11. The method according to claim 10, wherein the first reference point is recognized by using a marker attached onto a skin of the object when the pre-imaged medical image is generated.

12. The method according to claim 10, wherein, in the detecting of the movement of the user, a change in a sightline of the user is detected, and the image is changed based on the detected change in the sightline of the user.

13. The method according to claim 12, wherein, in the image to be displayed, the image is displayed in at least one from among a cross-sectional image and a cutaway image based on the detected change in the sightline of the user.

14. The method according to claim 10, wherein, in the detecting of the movement of the user, a change in a distance between the user and the object is detected, and
the image is enlarged as the detected distance between the user and the object decreases, and is reduced as the detected distance between the user and the object increases.

15. The method according to claim 10, wherein, in the registering the pre-imaged medical image with respect to the object, a first coordinate system based on the first reference point in the pre-imaged medical image and a second coordinate system based on the second reference point of the object are set and the first coordinate system is matched to the second coordinate system.

16. The method according to claim 10, wherein the displaying the image comprises displaying the image as an overlay on the object.

17. The method according to claim 10, wherein the pre-imaged medical image is a three-dimensional (3D) image and includes at least one from among a magnetic resonance imaging image, a computed tomography image, a single photon emission computed tomography image, a positron emission tomography image and an ultrasound image.

18. The method according to claim 10, further comprising displaying an image of the pre-imaged medical image that corresponds to an area of the object at which the diagnostic device is positioned, in response to the marker on the diagnostic device being detected.

* * * * *